US010881809B2

(12) United States Patent
Kwolek et al.

(10) Patent No.: US 10,881,809 B2
(45) Date of Patent: Jan. 5, 2021

(54) EXOSTRUCTURE TO ASSIST IN ACCURATE SYRINGE INJECTION

(71) Applicant: KB Medical, LLC, Las Vegas, NV (US)

(72) Inventors: Marilyn Kwolek, Danville, CA (US); Jon Block, San Francisco, CA (US)

(73) Assignee: KB Medical, LLC, Las Vegas, NV (US)

( * ) Notice: Subject to any disclaimer, the term of this patent is extended or adjusted under 35 U.S.C. 154(b) by 163 days.

(21) Appl. No.: 16/035,408

(22) Filed: Jul. 13, 2018

(65) Prior Publication Data

US 2019/0060576 A1     Feb. 28, 2019

Related U.S. Application Data

(60) Provisional application No. 62/548,640, filed on Aug. 22, 2017.

(51) Int. Cl.
*A61M 5/315* (2006.01)
*A61M 5/31* (2006.01)

(52) U.S. Cl.
CPC ........ *A61M 5/3158* (2013.01); *A61M 5/3137* (2013.01); *A61M 5/31515* (2013.01);
(Continued)

(58) Field of Classification Search
CPC .............. A61M 5/3158; A61M 5/3159; A61M 5/31593; A61M 5/31595; A61M 5/31515;
(Continued)

(56) References Cited

U.S. PATENT DOCUMENTS 2,491,978 A    12/1949  Helfman et al.
2,632,445 A     3/1953  Kas, Sr. et al.
(Continued)

FOREIGN PATENT DOCUMENTS

WO    WO-2008083875 A1    7/2008
WO    WO-2017001923 A1    1/2017
WO    WO-2019040228 A1    2/2019

OTHER PUBLICATIONS

"International Search Report for PCTUS2018043956 dated Oct. 2, 2018".

(Continued)

*Primary Examiner* — Tiffany Legette
*Assistant Examiner* — John J Crawford
(74) *Attorney, Agent, or Firm* — Wilson Sonsini Goodrich & Rosati

(57) ABSTRACT

A syringe exostructure includes a main body which removably receives a syringe having a syringe barrel and a syringe plunger. A drive plunger is reciprocatably mounted on the main body, and a plunger bar is slidably received in an axial channel on the drive plunger. The plunger bar is configured to removably couple to the syringe plunger when the syringe is introduced into the main body. A drive pawl assembly is fixed to an upper surface of the drive plunger and transfers forward motion of the drive plunger to the plunger bar as the drive plunger is advanced and disengages from the plunger bar when the drive plunger is retracted. A locking pawl assembly is fixed to the main body and extends through a slot formed in the bottom of the axial channel in the drive plunger. The locking pawl engages the plunger bar and allows the plunger bar to be advanced by the drive plunger as the drive plunger is advanced but prevents the plunger bar from being retracted by the drive plunger as the drive plunger is retracted.

5 Claims, 4 Drawing Sheets

(52) U.S. Cl.
CPC ... *A61M 5/31593* (2013.01); *A61M 2205/581* (2013.01); *A61M 2205/582* (2013.01)

(58) Field of Classification Search
CPC .......... A61M 5/31525; A61M 5/31526; A61M 5/31533; A61M 5/31537; A61M 5/3156; A61M 5/31566; A61M 5/31565; A61M 5/31578; A61M 5/3153; A61M 5/31; A61M 5/3137; A61M 5/178; A61M 2005/2411; A61M 3/3158; A61M 2205/581; A61M 2205/582
See application file for complete search history.

(56) References Cited

U.S. PATENT DOCUMENTS

| | | | |
|---|---|---|---|
| 3,110,310 A | 11/1963 | Frank et al. | |
| 4,022,207 A * | 5/1977 | Citrin | A61M 5/20 604/209 |
| 4,415,101 A | 11/1983 | Shapiro et al. | |
| 4,865,591 A * | 9/1989 | Sams | A61M 5/31553 604/186 |
| 5,722,956 A | 3/1998 | Sims et al. | |
| 6,699,224 B2 | 3/2004 | Kirchhofer et al. | |
| 8,851,336 B2 | 10/2014 | Weill et al. | |
| 8,936,578 B2 | 1/2015 | Cronenberg | |
| 2004/0019333 A1 | 1/2004 | Graf et al. | |
| 2007/0197976 A1 | 8/2007 | Jacobs et al. | |
| 2008/0103435 A1 | 5/2008 | Graf et al. | |
| 2014/0012229 A1 * | 1/2014 | Bokelman | A61M 5/24 604/506 |
| 2015/0025502 A1 * | 1/2015 | Spenser | A61M 5/31511 604/506 |
| 2016/0213854 A1 | 7/2016 | Schwab et al. | |
| 2019/0175839 A1 | 6/2019 | Kwolek et al. | |

OTHER PUBLICATIONS

International Search Report and Written Opinion for PCT/US2020/018889 dated May 19, 2020.

* cited by examiner

EXOSTRUCTURE TO ASSIST IN ACCURATE SYRINGE INJECTION

CROSS-REFERENCE TO RELATED APPLICATION

The present application claims the benefit of provisional application No. 62/548,640, filed on Aug. 22, 2017, the full disclosure of which is incorporated herein by reference.

BACKGROUND OF THE INVENTION

1. Field of the Invention

The present invention relates generally to the field of medical devices and methods. More specifically, the invention described herein relates to devices and methods for delivering doses of a medicament from a syringe to a patient.

Existing syringes utilize a plunger to push fluids out of a barrel through a needle and into an injection site. In the normal clinical setting, the practitioner's dominant free hand deploys the syringe with the thumb used to depress the plunger and the index and middle fingers placed on the flanges to provide direction and stabilization. Using the standard free-hand injection method, existing disposable syringes function well at delivering the total volume of the barrel as a single measured dose. However, a number of clinical interventions (e.g., botulinum toxin, deoxycholic acid, and hyaluronic acid) require that the contents of the syringe be apportioned reproducibly in separate, discrete units (i.e., doses) across multiple injection sites during the same procedure.

Free-hand injection is an inaccurate and imprecise technique for delivering discrete units at multiple sites during the same procedure with expediency. This practice carries a risk of administering an incorrect dose to an injection site, even for an experienced medical professional. The risk of administering an incorrect dose utilizing the same syringe can be due to several factors that include the change in thumb force on the plunger required to reproducibly extrude the same volume of a fluid from a syringe as well as measurement errors when attempting to visualize the barrel markings at different angles.

Therefore, a need exists for apparatus and methods for administering accurate volumetric units from a syringe filled with a medicament volume sufficient for multiple dosages.

2. Description of the Background Art

Background patents and publications include US2015025502; U.S. Pat. Nos. 4,415,101; 4,022,207; and 2,491,978.

SUMMARY OF THE INVENTION

In a first aspect, the present invention provides a syringe exostructure intended to receive a conventional syringe and needle assembly which is either pre-filled or adapted to be filled with a medicament, such as but not limited to botulinum toxin, deoxycholic acid, and hyaluronic acid, to be delivered to a patient in multiple, sequential small aliquots or doses, usually having a volume in a range from 0.01 ml to 0.1 ml, typically from 0.025 ml to 0.05 ml. A total number of small aliquots or doses may be in the range from 10 to 100, typically from 20 to 40, and the syringe may carry a total volume of medicament in the range from 0.3 ml to 10.0 ml.

In exemplary embodiments, the syringe exostructure comprises a main body configured to removably receive a syringe having a syringe barrel and a syringe plunger. A drive plunger is reciprocatably mounted on the main body, and a plunger bar is slidably received in an axial channel on the drive plunger. The drive plunger is configured to removably couple to the syringe plunger when the syringe is introduced into the main body, and a drive pawl assembly is fixed to an upper surface of the drive plunger and is configured to transfer forward motion of the drive plunger to the plunger bar as the drive plunger is advanced and is further configured to disengage from the plunger bar when the drive plunger is retracted. A locking pawl assembly is fixed to the main body and extends through a slot formed in a bottom of the axial channel in the drive plunger and configured to engage the plunger bar and allow the plunger bar to be unidirectionally advanced by the drive plunger as the drive plunger is advanced but prevents the plunger bar from being retracted by the drive plunger as the drive plunger is retracted.

In specific embodiments of the syringe exostructure of the present invention, the drive pawl assembly comprises a pair of pawls forming a cam mechanism pivotally attached to the drive plunger and having tips configured to engage opposed inner surfaces of a channel formed in a bottom of the plunger bar. Usually, the tip of each pawl of the drive pawl assembly comprises a toothed or other surface configured to engage and drive a mating surface, typically a smooth plastic surface, on opposed inner sides of the channel formed in the bottom of the plunger bar. Typically, the engagement surface on each pawl engages with the mating surface on the inner surfaces of the channel as the drive plunger is advanced and disengages with the surface on the inner surfaces of the channel as the drive plunger is retracted.

In further specific embodiments of the syringe exostructure of the present invention the main body comprises a top shell having an upper surface with a barrel groove for removably receiving the syringe barrel and a bottom shell having an upper surface which carries the locking pawl assembly. The main body may further comprise a hinged cover for enclosing the syringe barrel when placed in the barrel groove.

In other exemplary embodiments, a syringe exostructure constructed in accordance with the principles of the present invention may comprise a main body front having a barrel groove, a flange slot, and a plunger shroud. A plunger bar comprises a plunger button mount, a set of locking teeth, and a set of driving teeth. The plunger comprises a plunger head, a plunger spring, a set of driving pawls, a paw spring, and a fastener. A main body back comprises a locking pawl and a spring mount. The barrel groove may be enclosed by a hinged door attached to the main body front, and the plunger button mount may be moveably positioned between the flange slot and the plunger head. The plunger shroud may be positioned between the flange slot and the plunger head, and the set of driving teeth may be detachably coupled to the set of driving pawls by way of the pawl spring. The plunger spring may be elastically engaged to the spring mount opposite the plunger head, and the locking pawl may be detachably coupled to the set of locking teeth.

In further exemplary embodiments, distance between the plunger head and the plunger shroud corresponds to distance traveled by the locking pawl between each tooth of the set of locking teeth, and the syringe exostructure may still further comprise a protruding structure surrounding the flange slot.

In further aspects of the present invention, systems may have any and/or all of the permutations and combinations of features as described previously.

BRIEF DESCRIPTION OF THE DRAWINGS

To easily identify the discussion of any particular element or act, the most significant digit or digits in a reference number refer to the figure number in which that element is first introduced.

DETAILED DESCRIPTION OF THE INVENTION

A syringe exostructure device to assist in the accurate delivery of individual units from a standard, single-use, disposable syringe filled with multiple doses. The syringe exostructure is single-use and disposable, and can be configured to support different syringe sizes and dosing requirements. The syringe exostructure includes formed features that ergonomically replicate the impression of a standard syringe. The syringe exostructure retains a syringe in place while a cam mechanism advances the syringe's plunger a set distance into the barrel to expel a measured volume with each compression of the exoskeleton plunger. Tactile and/or audible feedback(s) are provided when the plunger is compressed. The filled syringe is retained within a main body of the syringe exostructure and secured in place by the formed features and a hinged door that closes permanently and is tamper proof.

The plunger button of the syringe engages a plunger bar that advances a set distance towards the flange and the barrel when the plunger is compressed. The advancement of the plunger bar is driven by a set of driving pawls connected to the plunger that rake the plunger bar forward then disengage to return with the plunger to their starting position and reengage plunger bar closer to the plunger button. The distance traveled by the plunger head to the plunger shroud corresponds to the distance traveled by the locking pawl between each tooth of the set of locking teeth. During each advancement of the plunger bar, a locking pawl disengages the plunger bar and reengages when the plunger returns to the starting position, preventing the plunger bar from reversing direction. When the contents of the syringe have been expelled, the entire exostructure with syringe intact is discarded and cannot be reused.

A syringe exostructure in one aspect includes a main body front with a barrel groove, flange slot, and a plunger shroud; a plunger bar with a plunger button mount; a set of locking teeth; and a set of driving teeth. The plunger used with the syringe exostructure includes a plunger head, a plunger spring, a set of driving pawls, a pawl spring, and a fastener coupling: the pawl spring and the set of driving pawls to the plunger. A main body back portion of the exostructure includes a locking pawl and a spring mount.

The barrel groove is enclosably aligned to a hinged door attached to the main body front, and the plunger button is moveably positioned between the flange slot and the plunger head. The plunger shroud is positioned between the flange slot and the plunger head. The driving pawls are attached to the plunger by a fastener and have toothed surfaces which engage driving teeth on the plunger bar. The locking pawl is detachably coupled to the set of locking teeth.

Figure 1:
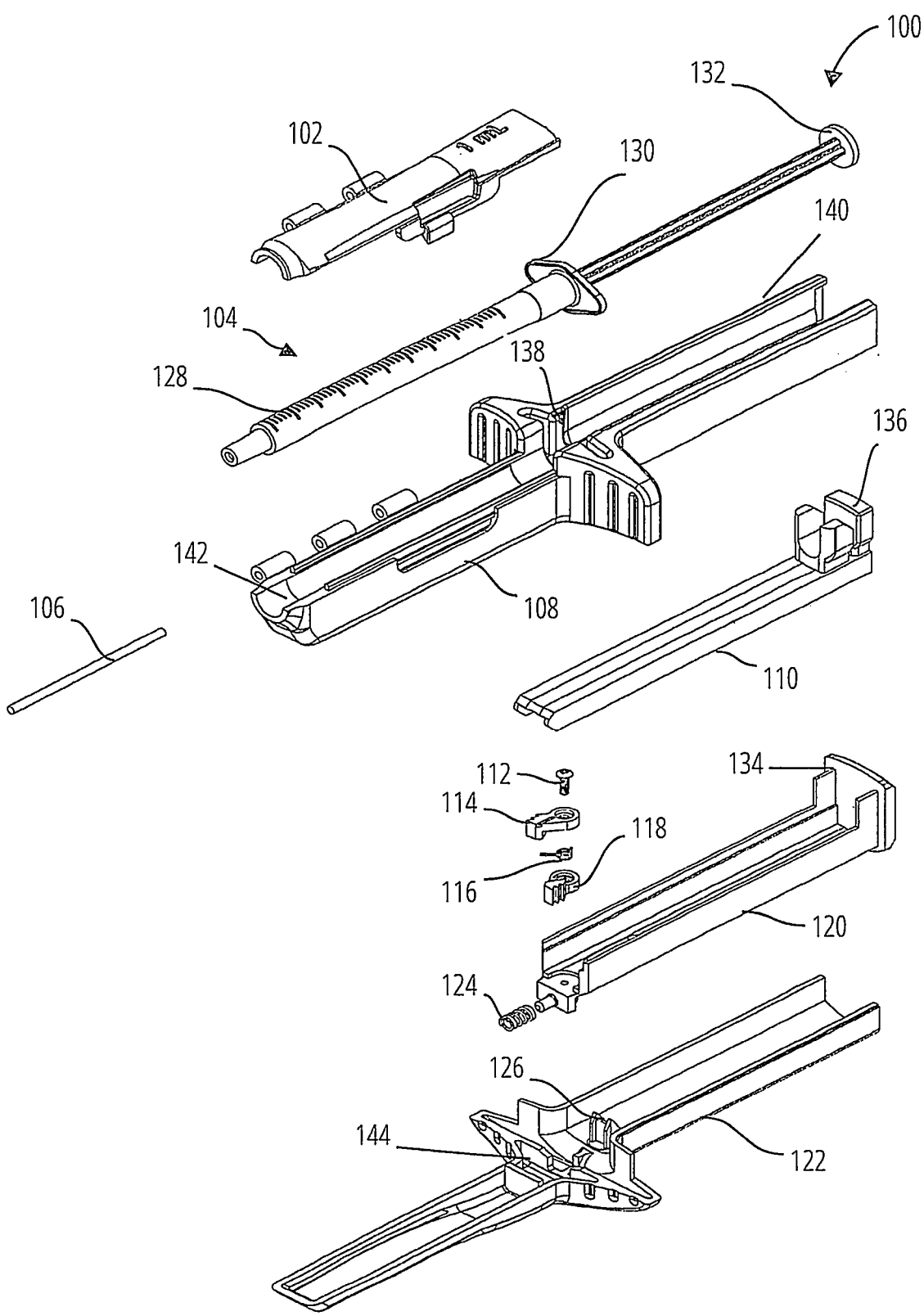
FIG. 1 illustrates an embodiment of a syringe exostructure constructed in accordance with the principles of the present invention shown in an exploded view.

Referencing FIG. 1, a syringe exostructure 100 includes a door 102, a hinge pin 106, a main body front 108, a plunger bar 110, a fastener 112, a first driving pawl 114, a pawl spring 116, and a second driving pawl 118. A plunger 120 includes a plunger head 134, and a main body back 122 includes a locking pawl 126 and a spring mount 144. The plunger bar 110 includes a plunger button mount 136. The main body front 108 includes a barrel groove 142, flange slot 138, and a plunger shroud 140.

The syringe exostructure 100 engages a standard disposable syringe 104 that includes a barrel 128, a flange 130, and a plunger button 132. The syringe exostructure 100 delivers a highly controlled volume of fluid from a syringe 104 upon compression of the plunger 120. The main body front 108 includes a formed cavity to receive the syringe 104. The formed cavity includes structures for retaining the flange 130 and barrel 128 of the syringe 104. The flange slot 138 is surrounded by protruding structures resembling an enlarged version of the flange 130. The main body front 108 includes hinges for mounting a door 102 adjacent to the barrel of the syringe 104. The hinges of the door 102 and the main body front 108 are secured through a hinge pin 106. While secured with the hinge pin 106, the door 102 swings to enclose the barrel 128 of the syringe 104 within the formed cavity of the main body front 108.

The plunger bar 110 engages the plunger button 132 of the syringe 104. The plunger bar 110, the plunger 120, and main body back 122 are coincidently aligned along the length of the syringe 104. The plunger bar 110 is operatively coupled to the plunger 120 through a first driving pawl 114 and a second driving pawl 118, as well as to a main body back 122 through a locking pawl 126. The first driving pawl 114 and the second driving pawl 118 are mounted to the plunger 120 through a fastener 112. The first driving pawl 114 and the second driving pawl 118 elastically engage the plunger bar 110 by way of a pawl spring 116. The plunger head 134 of the plunger 120 protrudes from the main body back 122. The plunger 120 is elastically coupled to the main body back 122 through a plunger spring 124. The locking pawl 126 of the main body back 122 traverses a slotted opening (not shown) through the bottom of the plunger 120 to engage the plunger bar 110 on a side opposite the syringe 104.

During operation of the syringe exostructure 100, the plunger head 134 is pushed in towards the main body back 122 until the plunger head 134 is coincident with the main body back 122. Movement of the plunger head 134 towards the main body back 122 extrudes the fluid from the barrel 128 of the syringe 104. The extrusion occurs when the first driving pawl 114 and the second driving pawl 118 move the plunger bar 110 to drive the plunger button mount 136 towards the flange 130, pushing the plunger button 132 into the barrel 128. The first driving pawl 114 and the second driving pawl 118 drive the movement of the plunger bar 110 towards the flange 130 and reposition the locking pawl 126 closer to the plunger button 132 during compression of the plunger spring 124.

When the plunger head 134 is released, the pawl spring 116 compresses, allowing the first driving pawl 114 and the second driving pawl 118 to move up the length of the plunger bar 110 towards the plunger button 132 as the plunger 120 returns to the starting position. The plunger bar 110 is kept in place relative to the movement of the plunger 120 through the engagement of the locking pawl 126. The travel distance of the plunger head 134 towards the main body back 122 is a set distance consistent with the travel distance of the locking pawl 126 along the plunger bar 110, resulting in a consistent volume extruded for each compression of the plunger head 134. The locking pawl 126 typically engages a toothed or "ratcheted" surface formed on the bottom of the plunger bar 110 to allow advancement of the plunger bar as the plunger is 120 is depressed and prevent retraction of the plunger bar as the plunger returns to its initial position. Usually, the locking pawl 126 will also provide audible and/or tactile feedback as the toothed or ratcheted bottom of plunger bar 120 is advanced by the plunger 110 over the locking pawl.

Figure 2:
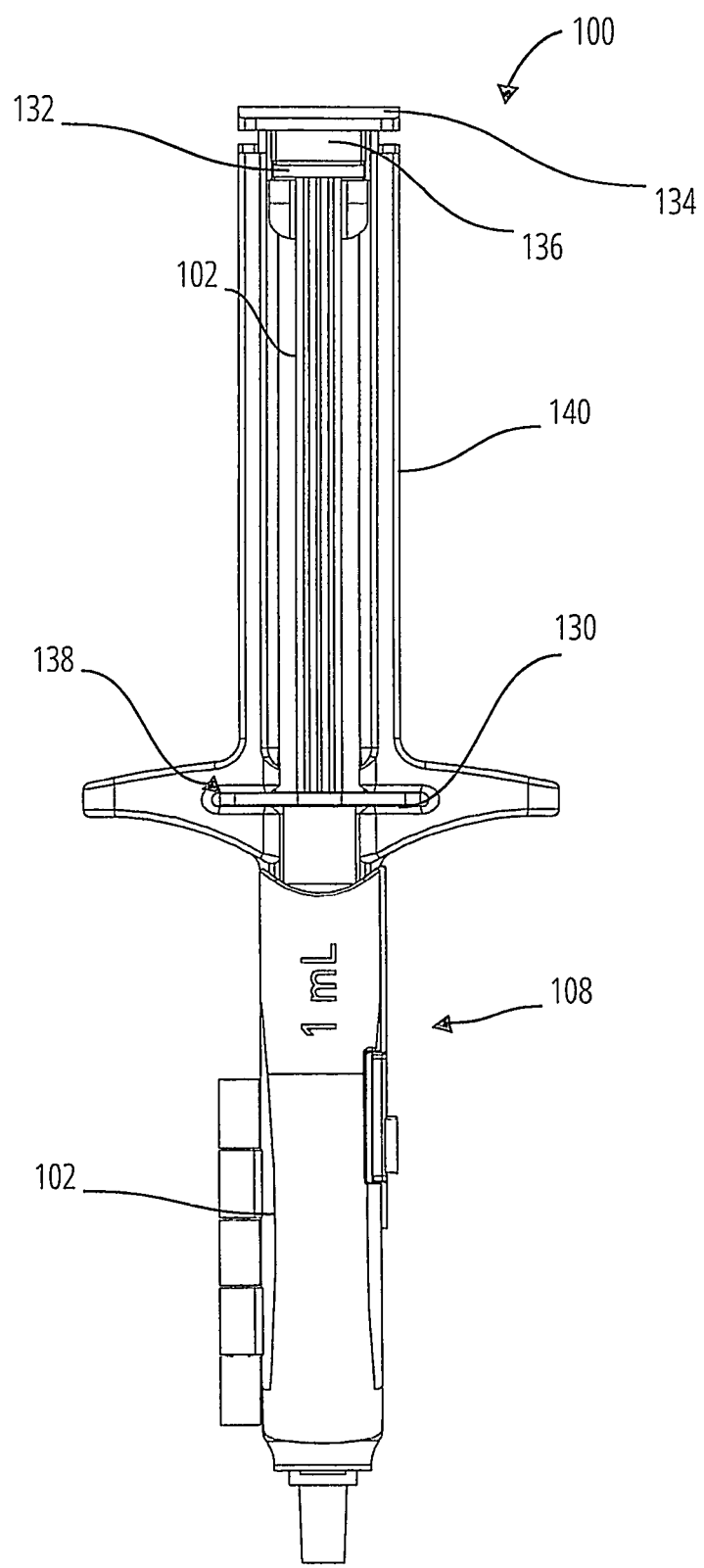
FIG. 2 illustrates a top view of the syringe exostructure of FIG. 1.

FIG. 2 illustrates a front view of an embodiment of a syringe exostructure 100, and shows the door 102, the main body front 108, the flange 130, the plunger button 132, the plunger head 134, the plunger button mount 136, the flange slot 138, and the plunger shroud 140.

Figure 3:
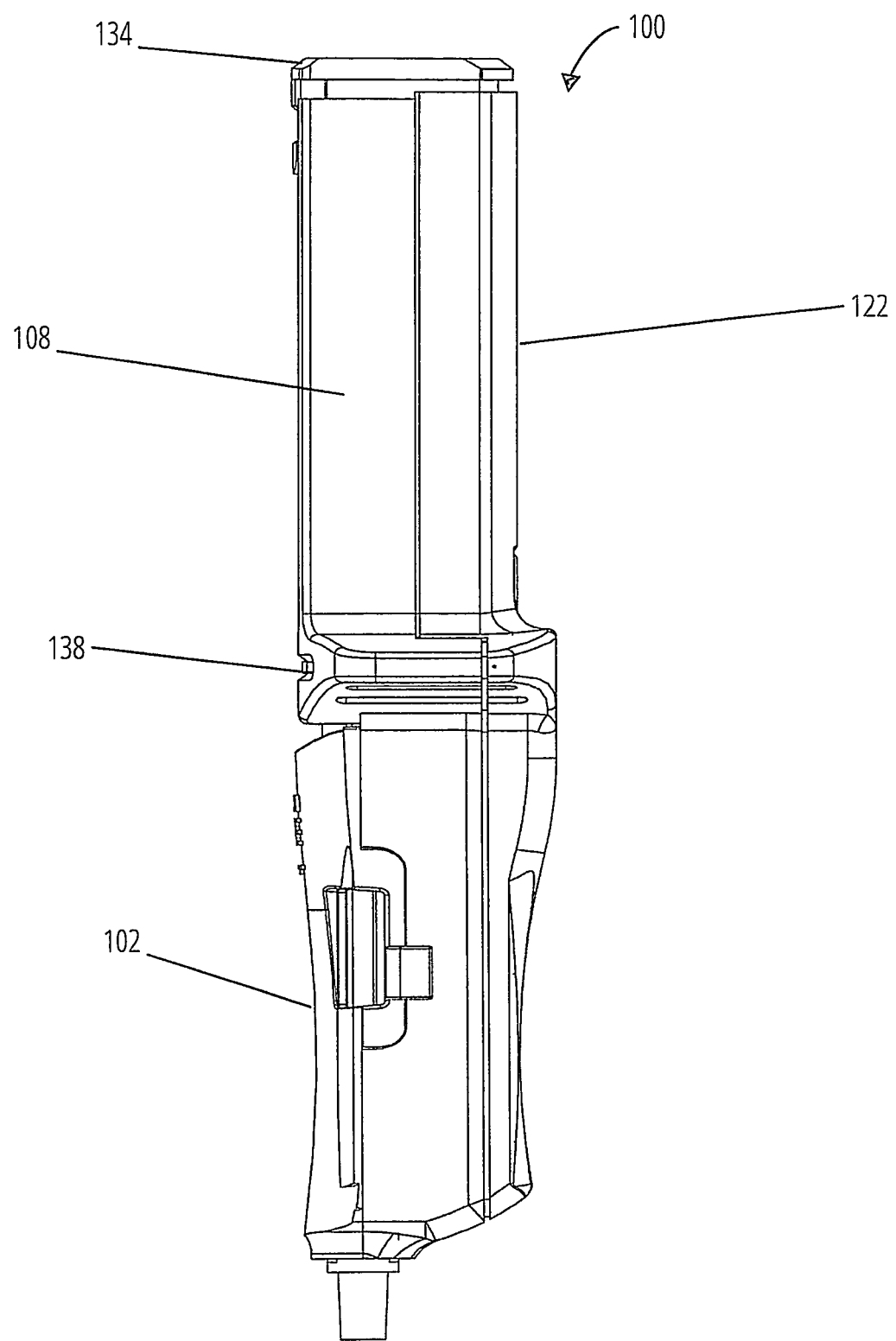
FIG. 3 illustrates a lateral view of the syringe exostructure of FIG. 1.

FIG. 3 illustrates a lateral view of the syringe exostructure 100, and shows the door 102, the main body front 108, the main body back 122; the plunger head 134, and the flange slot 138.

Figure 4:
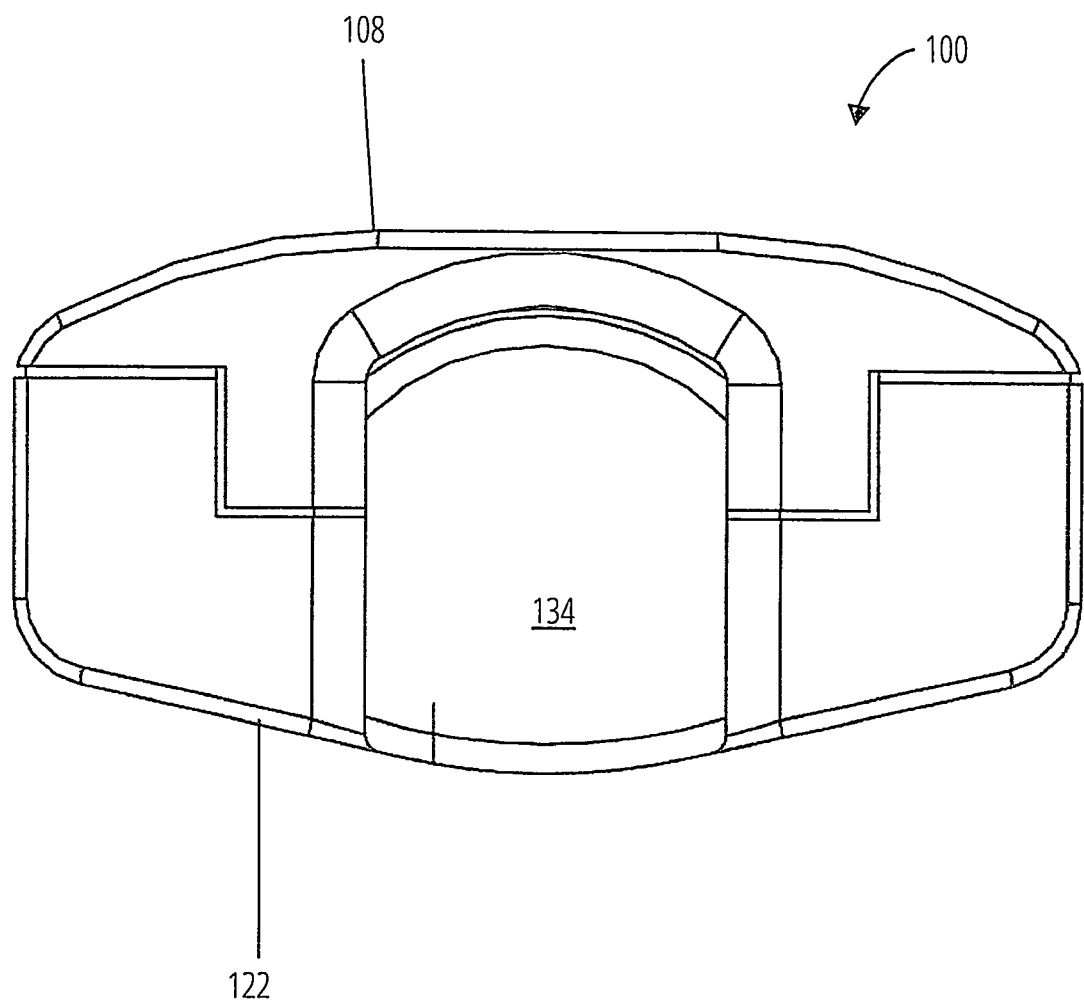
FIG. 4 is a view of a proximal or "plunger" end of the syringe exostructure of FIG. 1.

FIG. 4 illustrates a top elevational view of an embodiment of the syringe exostructure 100, showing the main body front 108, the main body back 122, and the plunger head 134.

The foregoing examples are not intended to limit the scope of the invention. All modifications, equivalents and alternatives are within the scope of the invention.

What is claimed is:

1. A syringe exostructure comprising:
   a main body configured to removably receive a syringe having a syringe barrel and a syringe plunger;
   a drive plunger reciprocatably mounted on the main body;
   a plunger bar slidably received in an axial channel on the drive plunger and configured to removably couple to the syringe plunger when the syringe is introduced into the main body;
   a drive pawl assembly fixed to an upper surface of the drive plunger and configured to transfer forward motion of the drive plunger to the plunger bar as the drive plunger is advanced; and
   a locking pawl assembly fixed to the main body and extending through a slotted opening formed in a bottom of the axial channel on the drive plunger and configured to engage the plunger bar and allow the plunger bar to be advanced by the drive plunger as the drive plunger is advanced but prevents the plunger bar from being retracted by the drive plunger as the drive plunger is retracted.

2. A syringe exostructure as in claim 1, wherein the drive pawl assembly comprises a pair of pawls forming a cam mechanism pivotally attached to the drive plunger, said pawls being configured to engage opposed inner surfaces of a channel formed in a bottom of the plunger bar.

3. A syringe exostructure as in claim 2, wherein each pawl of the drive pawl assembly comprises a toothed surface configured to engage a toothed surface formed on the inner surfaces of the channel formed in the bottom of the plunger bar, wherein the toothed surface on each pawl engages with the toothed surface on the inner surfaces of the channel formed in the bottom of the plunger bar as the drive plunger is advanced and disengages with the toothed surface on the inner surfaces of the channel as the drive plunger is retracted.

4. A syringe exostructure as in claim 1, wherein the main body comprises a top shell having an upper surface with a barrel groove for removably receiving the syringe barrel and a bottom shell having an upper surface which carries the locking pawl assembly.

5. A syringe exostructure as in claim 4, wherein the main body further comprises a hinged cover for enclosing the syringe barrel when placed in the barrel groove.

* * * * *